(12) United States Patent
Bates et al.

(10) Patent No.: US 8,398,957 B2
(45) Date of Patent: Mar. 19, 2013

(54) AEROSOL COMPOSITIONS

(75) Inventors: Chris Bates, Eroy (GB); Erin Corstanje, Hull (GB); Chris Jones, Montvale, NJ (US); Maud Portier, Hull (GB); Hannah Tipple, Hull (GB)

(73) Assignee: Reckitt Benckiser (UK) Limited, Slough, Berkshire (GB)

( * ) Notice: Subject to any disclaimer, the term of this patent is extended or adjusted under 35 U.S.C. 154(b) by 809 days.

(21) Appl. No.: 12/247,386

(22) Filed: Oct. 8, 2008

(65) Prior Publication Data

US 2009/0098060 A1    Apr. 16, 2009

(30) Foreign Application Priority Data

Oct. 11, 2007   (GB) .................................. 0719848.4

(51) Int. Cl.
*A61K 9/00*   (2006.01)
*A61K 9/12*   (2006.01)

(52) U.S. Cl. ............ 424/43; 424/45; 424/400; 424/600; 424/646; 424/660

(58) Field of Classification Search .................... 424/43, 424/45, 400, 600, 646, 660
See application file for complete search history.

(56) References Cited

U.S. PATENT DOCUMENTS

| | | | | |
|---|---|---|---|---|
| 3,491,918 A | * | 1/1970 | Lucas | 222/635 |
| 4,313,837 A | * | 2/1982 | Vukasovich et al. | 508/170 |
| 5,951,993 A | * | 9/1999 | Scholz et al. | 424/405 |
| 2005/0159330 A1 | * | 7/2005 | Shah et al. | 510/504 |

\* cited by examiner

*Primary Examiner* — James H. Alstrum-Acevedo
(74) *Attorney, Agent, or Firm* — Norris McLaughlin & Marcus PA

(57) ABSTRACT

An aerosol composition comprising: 0.01 wt % to 1.00 wt % sodium borate; 0.01 wt % to 1.50 wt % polyglycerol ester surfactant; <30 wt % propellant; and 67.5 wt % to 85.0 wt % water. Methods of manufacture of an aerosol air freshener are also described wherein the aerosol composition further comprises a fragrance.

18 Claims, No Drawings

AEROSOL COMPOSITIONS

The present invention relates to aerosol compositions, a device comprising such compositions and a method of prevention of corrosion using said compositions.

Many products designed for use in household applications, on hard surfaces, for fabric care, as carpet cleaners are sold in aerosol containers. A few aerosol products are sold in glass or plastic containers. Most containers are metal canisters, most canisters are steel, usually tin coated, others are aluminium (which are the most expensive). Tin coated metal canisters may also be lacquered with a resin on the inside to provide additional protection.

Examples of aerosol products are air fresheners, car products, household products, fabric care, waxes, polishes, insecticides, ironing aids, fabric refreshers, and carpet cleaners.

Tin coating protects the metal canisters against rapid corrosion, but tends itself to dissolve in aqueous based formulations. With aerosol formulations containing less than 50 ppm of water, corrosion of tin plated canisters is not generally a serious problem. However, if the water content of an aerosol product is more than 50 ppm (and particularly when greater than 150 ppm), problems due to corrosion are more likely to occur.

The world market trend is to move towards water based aerosol formulations. This is due mainly to a regulatory issue; the reductions of the volatile organic content (VOC) levels in aerosol product has involved the reduction of the solvent level in many products and an increase of the water content. Currently it is desirable to have a propellant level of below 30% w/w not only to reduce cost but also to comply with increasingly stringent regulatory limits (e.g. a maximum of 24.5% w/w in the USA for air freshener products).

Many corrosion inhibitor systems have been developed for the new market requirements in aerosol products, especially for tin plated canisters. Examples of these products are borates, benzoates, molybdates, and anionic surfactants (such as sodium lauroyl sarcosinate).

Historically the common 'wet' (i.e. water rather than solvent based) air freshener aerosol compositions typically contain nitrite as a corrosion inhibitor and sorbitan monooleate as an emulsifier to ensure uniform emulsification of water soluble and oily components such as water insoluble fragrance. The best recognised inhibitor system for tin plated canisters is sodium nitrite and morpholine. Morpholine is a volatile base that helps to preserve the vapour phase in the aerosol containers and gives an alkaline pH to the formula. This system can involve the formation of nitrosamines that are very carcinogenic.

In addition, even sodium nitrite and morpholine are not generally able to prevent the dissolution of the tin coating, but to reduce the rate of dissolution of the tin coating to an acceptable level. The amount of morpholine, sodium nitrite and thickness of tin plate are designed for around the required shelf life, for example two years. The dissolution of the tin plate to form a tin hydroxyl-oxide complex has been shown to have a negative effect on cleaning performances. The tin complex generally gives a pale yellow to an intense yellow colour when deposited, especially when sprayed onto a white surface. White fabrics or carpets can remain coloured by the liquids of aged aerosol products. Other considerations relate to certain stains like coffee, tea and wine that contain cationic metals. These metals can form brown coloured complex with tin hydroxyl-oxide complex, causing an evident negative effect of the cleaning formulation and its overall cleaning performance.

Even resin lacquered tin-plated canisters generally need an effective corrosion system. Possible defects on the lacquer layer are the cause of pit corrosion: where a galvanic potential is discharged in a limited area, involving a quick and deep corrosion. Even sodium nitrite and morpholine cannot prevent dissolution of the lacquer and tin plate, whereupon the liquid becomes yellowish and the interior can darken. This system is in addition to be avoided for nitrosamine formation during the product life.

It is desirable to replace nitrite corrosion inhibitors due to these health concerns and performance issues. One solution to this has been to replace nitrite corrosion inhibitors with phosphate corrosion inhibitors but these carry the financial penalty of requiring internally lacquered cans to obtain satisfactory storage/corrosion performance.

Many corrosion inhibitors have been identified in the prior art, but are not able to stop the dissolution of the tin layer in a tin plated aerosol canister over the two year standard canister life.

It has been found that a borate salt (such as sodium borate) alone or in combination with a molybdate salt (such as sodium molybdate) is particularly effective.

However when using sodium borate as a corrosion inibitor it has been discovered that standard emulsifiers such as sorbitan monooleate used in combination with sodium borate at propellant (butane/propane) levels of below 30% w/w results in very coarse particle sizes and excessive foaming, making the product unsuitable as an aerosol air freshener.

According to a first aspect of the present invention, there is provided an aerosol composition comprising:
0.01 wt % to 1.00 wt % sodium borate;
0.01 wt % to 1.50 wt % polyglycerol ester surfactant;
<30 wt % propellant; and
67.5 wt % to 85.0 wt % water.

For the avoidance of doubt, the term "polyglycerol ester" is used herein to designate esters of diglycerols, triglycerols as well as polyglycerols and/or combinations thereof.

Preferably the aerosol composition further comprises 0.01 wt % to 0.5 wt % sodium molybdate, and even more preferably comprises 0.01 wt % to 0.1 wt % sodium molybdate.

In a preferred aspect of the present invention, the aerosol composition as hereinbefore described comprises a polyglycerol ester surfactant selected from the group comprising polyglycerol esters of $C_{12}$ to $C_{24}$ fatty acids. In an especially preferred embodiment, the polyglycerol ester surfactant comprises the polyglycerol ester of oleic acid or stearic acid or a mixture thereof.

It has been surprisingly found that a combination of diglycerol ester surfactants with borate corrosion inhibitor systems provides acceptably fine particle sizes without foaming while also meeting requirements such as low toxicity and low corrosivity towards aerosol cans. This unexpected discovery avoids almost all the negative defects of the existing corrosion inhibitors.

In a further preferred aspect of the present invention, the aerosol composition as hereinbefore described comprises a propellant which is a hydrocarbon, preferably butane or propane or a mixture thereof, especially butane including but not limited to grades 31, 40, 46 and 70 (where the number relates to the pressure in psig at a temperature of 70° F.).

In a yet further aspect of the present invention, there is provided an aerosol composition as hereinbefore described which further comprises an organic solvent, preferably an alcohol such as ethanol or similar solvent.

Preferably the aerosol composition as hereinbefore described further comprises a fragrance in the range 0.1 wt % to 5 wt %.

Preferably the aerosol composition according to the present invention comprises 0.2 wt % to 0.7 wt % sodium borate, and most preferably 0.25 wt % to 0.50 wt %.

Preferably the aerosol composition according to the present invention comprises 0.1 wt % to 1.0 wt % of the polyglycerol ester surfactant, more preferably 0.25 wt % to 0.75 wt %, and most preferably 0.4 wt % to 0.6 wt %.

Preferably the aerosol composition according to the present invention comprises between 10 wt % to 30 wt % propellant, even more preferably 14 wt % to 28 wt % propellant, and most preferably 17 wt % to 27.5 wt %.

In an especially preferred embodiment of the present invention, there is provided an aerosol composition as hereinbefore described which comprises:

0.25 wt % to 0.50 wt % sodium borate;

0.05 wt % to 0.10 wt % sodium molybdate 0.1 wt % to 1.0 wt % polyglycerol ester surfactant;

17 wt % to 27.5 wt % propellant; and 70.5 wt % to 82.6 wt % water.

In a second embodiment of the present invention, there is provided an aerosol spray device containing a composition according to the first aspect of the present invention.

According to a third aspect of the present invention there is provided an aerosol air freshener containing a composition comprising 0.1 wt % to 5 wt % of a fragrance in combination with a composition according to the first aspect of the present invention. Preferably the aerosol air freshener composition comprises 0.1 wt % to 1 wt % of a fragrance in combination with a composition according to the first aspect of the present invention, and most preferably comprises 0.15 wt % to 0.35 wt % of said fragrance.

In a fourth embodiment of the present invention, there is provided a method of manufacture of an aerosol air freshener containing a composition according to the third aspect of the present invention, the method comprising the steps of:

preparing an aqueous phase premix of water and sodium borate;

preparing an oil phase premix of the fragrance and polyglycerol ester surfactant;

adding the premixes to an aerosol container; and then one of the following steps of:

crimping said aerosol container and then filling said container with propellant; or filling said container with propellant and then crimping said aerosol container.

Preferably the aqueous phase premix is also includes sodium molybdate.

In a fifth embodiment of the present invention, there is provided a method of preventing corrosion of aerosol containers wherein the method involves the step of introducing a composition according to the first or third aspect of the present invention into said aerosol container.

The following description and examples are intended merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

EXAMPLE 1

An aerosol air freshener formulation as follows:

| Description | % w/w |
| --- | --- |
| DI water | 74.21 |
| Sodium Borate | 0.37 |
| Sodium Molybdate | 0.08 |
| Fragrance | 0.25 |
| Emulsogen OG ™ | 0.50 |
| Propylene Glycol | 0.09 |
| Butane 46 | 24.50 |
| Total | 100.00 |

EXAMPLE 2

An aerosol air freshener formulation as follows:

| Description | % w/w |
| --- | --- |
| DI water | 74.29 |
| Sodium Borate | 0.37 |
| Fragrance | 0.25 |
| Emulsogen OG ™ | 0.50 |
| Propylene Glycol | 0.09 |
| Butane 46 | 24.50 |
| Total | 100.00 |

EXAMPLE 3

An aerosol air freshener formulation as follows:

| Description | % w/w |
| --- | --- |
| DI water | 71.21 |
| Sodium Borate | 0.37 |
| Sodium Molybdate | 0.08 |
| Fragrance | 0.25 |
| Emulsogen OGP ™ | 0.50 |
| Butane 40 | 27.50 |
| Total | 100.00 |

EXAMPLE 4

An aerosol air freshener formulation as follows:

| Description | % w/w |
| --- | --- |
| DI water | 71.29 |
| Sodium Borate | 0.37 |
| Fragrance | 0.25 |
| Emulsogen OGP ™ | 0.59 |
| Butane 40 | 27.50 |
| Total | 100.00 |

EXAMPLE 5

An aerosol air freshener formulation as follows:

| Description | % w/w |
|---|---|
| DI water | 81.66 |
| Sodium Borate | 0.41 |
| Sodium Molybdate | 0.09 |
| Fragrance | 0.25 |
| Emulsogen OGP ™ | 0.59 |
| Butane 40 | 17.00 |
| Total | 100.00 |

EXAMPLE 6

An aerosol air freshener formulation as follows:

| Description | % w/w |
|---|---|
| DI water | 81.75 |
| Sodium Borate | 0.41 |
| Fragrance | 0.25 |
| Emulsogen OGP ™ | 0.59 |
| Butane 40 | 17.00 |
| Total | 100.00 |

Emulsogen OG™ is an oleic acid polyglycerine ester emulsifier available from Clariant. Emulsogen OGP™ is an oleic acid polyglycerine ester emulsifier premixed with propylene glycol available from Clariant.

The above components were filled into a typical 3 piece tinplate aerosol can with an optimised valve and actuator combination.

All of the examples produced a two-layered (dual-phase) oil/water composition in the can. On agitation of the can a temporary mixture of the layers is achieved which will improve the spray performance of the aerosol.

Examples 1-4 were prepared and stored for 24 weeks at 5° C., 25° C. and 40° C. along with 6 weeks storage at 50° C. In all cases the cans sprayed correctly after storage and exhibited only minor de-tinning or surface rust with no significant corrosion that would endanger the cans integrity under normal storage conditions.

The same formulation was tested for spray properties with the following results:

|  | Particle size DV(50) (μm) | Spray Rate (g/s) |
|---|---|---|
| 100% full | 40-65 | 1.2-2.4 |
| 50% remaining | 50-75 | above 0.9 |
| 25% remaining | 60-100 | above 0.9 |

Residue on exhaustion < 5% w/w

All of the values are acceptable for use as an aerosol air freshener.

Examples 5 & 6 were prepared and stored for 6 weeks at 25° C. and 40° C. In all cases the cans sprayed correctly after storage and exhibited only minor de-tinning or surface rust with no significant corrosion that would endanger the cans integrity under normal storage conditions.

The same formulation was tested for spray properties with the following results:

|  | Particle size DV(50) (μm) | Spray Rate (g/s) |
|---|---|---|
| 100% full | 40-65 | 1.2-2.4 |
| 50% remaining | 50-75 | above 0.9 |
| 25% remaining | 60-100 | above 0.9 |

Residue on exhaustion < 5% w/w

All of the values are acceptable for use as an aerosol air freshener.

The invention claimed is:

1. An aerosol air freshener composition comprising:
   0.01 wt % to 1.00 wt % sodium borate;
   0 wt % to 0.5 wt % sodium molybdate;
   0.01 wt % to 1.50 wt % polyglycerol ester surfactant;
   0.1 wt % to 5 wt % fragrance;
   10 wt % to <30 wt % propellant; and
   67.5 wt % to 85.0 wt % water;
   wherein the composition comprises not more than 0.09% wt, of an organic solvent.

2. The aerosol air freshener composition according to claim 1, wherein the composition further comprises 0.01 wt % to 0.5 wt % sodium molybdate.

3. The aerosol air freshener composition according to claim 1, wherein the polyglycerol ester surfactant is selected from the group comprising polyglycerol esters of $C_{12}$ to $C_{24}$ fatty acids.

4. The aerosol air freshener composition according to claim 1, wherein the composition comprises 0.1 wt % to 1.0 wt % of the polyglycerol ester surfactant.

5. The aerosol air freshener composition according to claim 1, wherein the propellant is a hydrocarbon.

6. The aerosol air freshener composition according to claim 1, wherein the composition comprises 0.2 wt % to 0.7 wt % sodium borate.

7. The aerosol air freshener composition according to claim 1, wherein the composition comprises between 17 wt % to 27.5 wt % propellant.

8. The aerosol spray device containing the aerosol air freshener composition according to claim 1.

9. The aerosol air freshener composition according to claim 1, wherein the composition comprises 0.1 wt % to 1 wt % of a fragrance.

10. The aerosol air freshener composition according to claim 1, wherein the composition further comprises 0.01 wt % to 0.1 wt % sodium molybdate.

11. The aerosol air freshener composition according to claim 1 wherein the composition comprises 0.25 wt % to 0.75 wt % of the polyglycerol ester surfactant.

12. The aerosol air freshener composition according to claim 11 wherein the composition comprises 0.4 wt % to 0.6 wt % of the polyglycerol ester surfactant.

13. The aerosol air freshener composition according to claim 3 wherein the polyglycerol ester surfactant is selected from the group comprising the polyglycerol esters of oleic acid or stearic acid or a mixture thereof.

14. The aerosol air freshener composition according to claim 6 wherein the composition comprises 0.25 wt % to 0.50 wt % sodium borate.

15. The aerosol air freshener composition according to claim 1, wherein the composition is dispensed as a spray which includes particles within the range of 40-100 DV (50) micrometers.

16. A method of manufacture of an aerosol air freshener containing an aerosol air freshener composition according to claim 1, the method comprising the steps of:
- preparing an aqueous phase premix of water and sodium borate;
- preparing an oil phase premix of the fragrance and polyglycerol ester surfactant;
- adding the premixes to an aerosol container; and then one of the following steps of:
- crimping said aerosol container and then filling said container with propellant; or
- filling said container with propellant and then crimping said aerosol container.

17. A method of preventing corrosion of aerosol containers wherein the method involves the step of introducing a composition according to claim 1 into said aerosol container.

18. A method of manufacture of an aerosol composition containing an aerosol air freshener composition according to claim 1, the method comprising the steps of:
- preparing an aqueous phase premix which comprises water and sodium borate and when present, sodium molybdate;
- preparing an oil phase premix which comprises the fragrance and polyglycerol ester surfactant;
- adding the premixes to an aerosol container;
- and then one of the following steps of:
- crimping said aerosol container and then filling said container with propellant; or
- filling said container with propellant and then crimping said aerosol container.

* * * * *